(12) United States Patent
Radney (10) Patent No.: US 7,665,465 B2
(45) Date of Patent: Feb. 23, 2010

(54) HEADGEAR ASSEMBLY FOR A RESPIRATORY SUPPORT SYSTEM

(75) Inventor: Steven B. Radney, Pittsburgh, PA (US)

(73) Assignee: RIC Investments, LLC, Wilmington, DE (US)

( * ) Notice: Subject to any disclaimer, the term of this patent is extended or adjusted under 35 U.S.C. 154(b) by 80 days.

(21) Appl. No.: 11/090,472

(22) Filed: Mar. 25, 2005

(65) Prior Publication Data

US 2006/0213521 A1 Sep. 28, 2006

(51) Int. Cl.
*A62B 18/08* (2006.01)
(52) U.S. Cl. .................... 128/207.11; 128/205.25; 128/206.12; 128/206.13; 128/206.18; 128/206.21; 128/206.24; 128/206.27; 128/206.28
(58) Field of Classification Search ............ 128/207.11, 128/205.25, 206.12, 206.13, 206.18, 206.21, 128/206.24, 206.27, 206.28
See application file for complete search history.

(56) References Cited

U.S. PATENT DOCUMENTS

| | | | | |
|---|---|---|---|---|
| 853,439 | A * | 5/1907 | Clark | 128/207.18 |
| 1,081,745 | A * | 12/1913 | Johnston et al. | 128/203.25 |
| 1,926,027 | A * | 9/1933 | Biggs | 128/205.25 |
| 2,100,374 | A * | 11/1937 | Biever | 55/379 |
| 2,259,817 | A | 10/1941 | Hawkins | |
| 2,348,074 | A * | 5/1944 | Lambertsen | 128/205.17 |
| 2,837,090 | A * | 6/1958 | Bloom et al. | 128/206.24 |
| 3,978,854 | A | 9/1976 | Mills, Jr. | |
| 4,354,488 | A | 10/1982 | Bartos | |
| 4,367,735 | A | 1/1983 | Dali | |
| 4,782,832 | A | 11/1988 | Trimble et al. | |
| 4,919,128 | A | 4/1990 | Kopala et al. | |
| 4,938,209 | A | 7/1990 | Fry | |
| 5,042,478 | A | 8/1991 | Kopala et al. | |
| 5,241,954 | A | 9/1993 | Glenn | |
| 5,269,296 | A | 12/1993 | Landis | |
| 5,477,852 | A | 12/1995 | Landis et al. | |
| 5,517,986 | A * | 5/1996 | Starr et al. | 128/206.24 |
| 5,533,506 | A | 7/1996 | Wood | |
| 5,538,000 | A | 7/1996 | Rudolph | |
| 5,558,089 | A | 9/1996 | Castiglione | |
| 5,584,286 | A * | 12/1996 | Kippax | 128/200.24 |
| 5,724,965 | A | 3/1998 | Handke et al. | |
| 5,752,510 | A | 5/1998 | Goldstein | |
| 5,794,617 | A * | 8/1998 | Brunell et al. | 128/206.16 |

(Continued)

FOREIGN PATENT DOCUMENTS

WO WO 2004/018014 A2 3/2004

OTHER PUBLICATIONS

U.S. Appl. No. 10/918,832, filed Aug. 13, 2004, Ho et al.

(Continued)

*Primary Examiner*—Patricia Bianco
*Assistant Examiner*—Nihir Patel
(74) *Attorney, Agent, or Firm*—MIchael W. Haas (57) ABSTRACT

A respiratory support system having a patient interface attached to a headgear assembly for delivering a gas to a patient is disclosed. The headgear provides a rigid member and a pad held in place on the patient's head by straps. The rigid member functions to prevent creep of the straps, distribute the strapping forces, and minimized tangential strap forces that otherwise squeeze the sides of the patient's head.

20 Claims, 11 Drawing Sheets

U.S. PATENT DOCUMENTS

| | | | | |
|---|---|---|---|---|
| 5,921,239 A * | 7/1999 | McCall et al. | ......... | 128/205.25 |
| 6,012,455 A * | 1/2000 | Goldstein | ............. | 128/207.18 |
| 6,019,101 A * | 2/2000 | Cotner et al. | .......... | 128/207.13 |
| 6,044,844 A * | 4/2000 | Kwok et al. | ........... | 128/207.11 |
| 6,119,694 A * | 9/2000 | Correa et al. | .......... | 128/207.13 |
| 6,325,507 B1 | 12/2001 | Jannard et al. | | |
| 6,347,631 B1 * | 2/2002 | Hansen et al. | ......... | 128/207.11 |
| 6,422,238 B1 * | 7/2002 | Lithgow | ................ | 128/207.11 |
| 6,427,694 B1 * | 8/2002 | Hecker et al. | .......... | 128/206.21 |
| 6,431,172 B1 | 8/2002 | Bordewick | | |
| 6,463,931 B1 | 10/2002 | Kwok et al. | | |
| 6,497,232 B2 * | 12/2002 | Fecteau et al. | .......... | 128/207.11 |
| 6,516,802 B2 * | 2/2003 | Hansen et al. | ......... | 128/207.11 |
| 6,561,191 B1 | 5/2003 | Kwok | | |
| 6,588,424 B2 * | 7/2003 | Bardel | ................... | 128/207.11 |
| 6,595,214 B1 * | 7/2003 | Hecker et al. | .......... | 128/207.13 |
| 6,662,803 B2 * | 12/2003 | Gradon et al. | ......... | 128/205.25 |
| 6,712,072 B1 * | 3/2004 | Lang | ..................... | 128/206.27 |
| 6,789,543 B2 * | 9/2004 | Cannon | ................. | 128/207.18 |
| 6,854,465 B2 * | 2/2005 | Bordewick et al. | ..... | 128/207.11 |
| 6,926,004 B2 * | 8/2005 | Schumacher | ........... | 128/206.27 |
| 7,066,179 B2 * | 6/2006 | Eaton et al. | ............ | 128/206.27 |
| 7,089,941 B2 * | 8/2006 | Bordewick et al. | ..... | 128/207.11 |
| 7,357,136 B2 * | 4/2008 | Ho et al. | ................. | 128/207.11 |
| 2001/0015204 A1 | 8/2001 | Hansen et al. | ......... | 128/205.25 |
| 2002/0011248 A1 * | 1/2002 | Hansen et al. | ......... | 128/207.11 |
| 2002/0074001 A1 * | 6/2002 | Kwok et al. | ........... | 128/207.11 |
| 2002/0117177 A1 * | 8/2002 | Kwok | ..................... | 128/207.11 |
| 2002/0174868 A1 * | 11/2002 | Kwok et al. | ........... | 128/205.25 |
| 2003/0019496 A1 * | 1/2003 | Kopacko et al. | ....... | 128/206.24 |
| 2003/0062048 A1 * | 4/2003 | Gradon et al. | ......... | 128/207.11 |
| 2003/0075180 A1 * | 4/2003 | Raje et al. | .............. | 128/206.24 |
| 2003/0145857 A1 * | 8/2003 | Sullivan et al. | ........ | 128/205.25 |
| 2003/0154978 A1 * | 8/2003 | Gradon et al. | ......... | 128/204.18 |
| 2004/0025882 A1 * | 2/2004 | Madaus et al. | ......... | 128/206.27 |
| 2004/0025883 A1 * | 2/2004 | Eaton et al. | ............ | 128/206.27 |
| 2004/0035427 A1 * | 2/2004 | Bordewick et al. | ..... | 128/206.27 |
| 2004/0045551 A1 * | 3/2004 | Eaton et al. | ............ | 128/206.21 |
| 2004/0065328 A1 * | 4/2004 | Amarasinghe et al. | . | 128/206.27 |
| 2004/0118406 A1 * | 6/2004 | Lithgow et al. | ........ | 128/206.24 |
| 2004/0216746 A1 * | 11/2004 | Jones et al. | ............ | 128/206.21 |
| 2004/0221850 A1 * | 11/2004 | Ging et al. | ............. | 128/206.27 |
| 2004/0244799 A1 * | 12/2004 | Landis | ................... | 128/206.21 |
| 2005/0016544 A1 * | 1/2005 | Thornton | ............... | 128/207.18 |
| 2005/0039753 A1 * | 2/2005 | Schumacher | ........... | 128/206.27 |
| 2005/0056286 A1 * | 3/2005 | Huddart et al. | ........ | 128/206.21 |
| 2005/0072428 A1 * | 4/2005 | Ho et al. | ................. | 128/205.25 |
| 2005/0076913 A1 * | 4/2005 | Ho et al. | ................. | 128/206.27 |
| 2005/0145249 A1 * | 7/2005 | Solyntjes et al. | ....... | 128/205.25 |
| 2005/0155603 A1 * | 7/2005 | Frerichs et al. | ........ | 128/206.21 |
| 2005/0199241 A1 * | 9/2005 | Ging et al. | ............. | 128/207.11 |
| 2006/0042629 A1 * | 3/2006 | Geist | ..................... | 128/206.24 |
| 2006/0081250 A1 * | 4/2006 | Bordewick et al. | ..... | 128/206.11 |
| 2006/0090760 A1 * | 5/2006 | Gradon et al. | ......... | 128/206.27 |
| 2006/0100538 A1 * | 5/2006 | Genger et al. | ................ | 600/544 |
| 2006/0118119 A1 * | 6/2006 | Berthon-Jones et al. | | 128/207.11 |
| 2006/0185675 A1 * | 8/2006 | Colin | .................... | 128/206.24 |
| 2006/0201515 A1 * | 9/2006 | Kwok et al. | ........... | 128/206.24 |

OTHER PUBLICATIONS

Respironics, Inc., ComfortLite™, © 2004 Respironics, Inc. and its affiliates.

AEIOMed, Inc., aura™, AEIOMed, Inc.

PCT Search Report and Written Opinion, Jul. 24, 2007.

* cited by examiner

HEADGEAR ASSEMBLY FOR A RESPIRATORY SUPPORT SYSTEM

BACKGROUND OF THE INVENTION

1. Field of the Invention

The present invention relates to headgear assemblies, and, in particular, to headgear assemblies used in a respiratory support system to securely position gas delivery masks on a patient.

2. Description of the Related Art

There are numerous situations where it is necessary or desirable to deliver a flow of breathing gas, non-invasively, to the airway of a patient, i.e., without intubating the patient or surgically inserting a tracheostomy tube in their trachea. For example, it is known to ventilate a patient using a technique known as non-invasive ventilation. It is also known to deliver continuous positive airway pressure (CPAP) or variable airway pressure support system such as the BiPAP® device registered to RIC Investments, Inc., or an auto-titration pressure support system which varies with the patient's respiratory cycle or a monitored condition of the patient, to treat a medical disorder, such as sleep apnea syndrome, obstructive sleep apnea (OSA), congestive heart failure, stroke, Cheynes-Stokes respiration, diabetes, etc. In fact, pressure support therapies continue to be found to be of benefit in other medical disorders. Non-invasive ventilation and pressure support therapies involve the placement of a patient interface device, which is typically a nasal or nasal/oral mask, on the face of the patient to interface the ventilator or pressure support device with the airway of the patient, so that a flow of breathing gas can be delivered from the pressure/flow generating device to the airway of the patient.

Because such patient interface devices are typically worn for an extended period of time, two competing concerns must be balanced for effective treatment: comfort and seal integrity. When providing CPAP or other positive pressure therapy to treat OSA, the patient normally wears the patient interface device all night long while he or she sleeps. On one hand, in order to be effective in this application the patient interface device must be as comfortable as possible, otherwise patient compliance will be low thus defeating potential treatment effectiveness. Most patients find a loose fitting mask more comfortable than one that this cinched down tightly on their face. On the other hand, the patient interface must be tightened adequately to provide an airtight seal and prevent the patient interface from becoming misaligned. To further complicate matters, human facial geometry is rather complex about the patient's mouth and nose. This region includes rapidly varying contours. Moreover, the thickness of the soft tissue also varies from region to region about this region of the patient's face. The cheeks tend to be a region with thick soft tissue while the region about the patient's nose tends to have little soft tissue resulting in a comparatively hard region. In addition to these broad generalities, each patient's face is unique, thereby further complicating attempts to create a mask that is comfortable and effective for a wide variety of patients. What is comfortable and effective for one patient may prove to be entirely unsuitable for another.

Typically patient interface devices include a shell or support that is often rigid in construction that supports a mask cushion, mouthpiece, or nasal cannula. The cushion is usually formed from a deformable elastomeric material and directly contacts the patient. To form an airtight seal with the patient, the cushion deforms about the patient's facial contours. The patient interface is held in place by a headgear assembly that includes straps that are wrapped around the patient's head and cinched down to draw the interface firmly against the face of the user. One such headgear assembly exemplary of the art is described in U.S. Patent Application Publication No. US 2002/0117177 ("the '177 reference"). This reference discloses a nasal mask that is held in place by a pair of straps: an upper strap across the patient's forehead region and a second strap extending from the patient's nasal region. The straps are joined together at a coupling member and held in place by a rear webbing portion.

Although this device may operate adequately for its intended purpose, it has several drawbacks as well. For instance, in order to secure the mask on the user's face, the straps and webbing pull the mask inward. The amount of force needed to secure the mask in place far exceeds the amount of force needed to create an airtight seal. Doing so, concentrates a large amount of stress on the region about the patient's nose and mouth. Secondly, the amount of force needed to prevent the patient interface from becoming misaligned far exceeds the amount of force needed to create an airtight seal.

Finally, these patient interfaces have straps that encircle the patient's head. As a result, a force is exerted about the patient's head that squeeze the sides inwardly as the straps circumnavigate the rounded surface of the patient's head.

Another headgear assembly is described in U.S. Pat. No. 6,516,802 ("the '802 patent") that overcomes some of the above noted disadvantages. Rather than using straps that extend around the patient's head, this reference discloses a mounting member that is looped over the top of the patient's head along the sagittal suture and has a pad below the occipital bone. The pad creates a force to draw the mask into the patient's face.

Headgear assemblies constructed in accordance with the teachings of the '802 patent overcome some of the disadvantages found in the art. Unlike the '177 reference, this device does not extend about the sides of the patient's head. Instead this device loops over the top of the patient's head along the sagittal bone. These headgear assemblies hold the device in place by drawing the cushion inward to hold the patient interface in place thereby, as in the '177 reference, they still concentrate the headgear retaining forces through the mask. Secondly, these headgear assemblies still circumnavigate the patient's head along a substantially curved path following the contours of the patient's head. Furthermore, the use of a single mounting member looped over the patient's head provides even less stability than in the '177 reference. The headgear assembly disclosed in the '802 patent is even more likely to be misaligned if bumped.

In order to overcome some of the disadvantages of the above described headgear assemblies, a headgear assembly was suggested in U.S. patent application Ser. No. 10/918,832 (assigned to the assignee of the present invention and hereby incorporated by reference in its entirety) ("the '832 application"). The patient interface disclosed in this reference includes a mask secured to a headgear by a coupling member. The headgear is adjustable and has a forehead strap, a cross strap, and a rear strap or webbing. The patient interface described in this pending application enhances comfort and provides a superior seal. Rather than securing the patient interface in place by applying a force acting through the mask, this headgear assembly separates the headgear assembly retention from the mask seal. The headgear assembly is secured to the patient's head regardless of the force needed to create an adequate air seal between the patient interface and the patient's face. In fact, the headgear could be worn without even attaching a patient interface. By separating these two functions, the headgear may be appropriately tightened to secure the patient interface in place and the mask may be adjusted to apply sufficient pressure to provide the desired seal with the patient. Neither the headgear nor the mask needs to be over tightened or under tightened to accommodate the requirements of the other feature.

Although such a device has certainly advanced the art, even this design could still be further improved upon. For instance, this device separates the headgear retention forces from the mask seal forces. Yet, this mask still concentrates the headgear strapping forces along the straps rather than dispersing it about the patient's head. In addition, the headgear assembly, as in the prior references, circumnavigates the patient's head about a curved path that results in squeezing inwardly on the patient's head as the headgear assembly is tightened. An additional feature of this invention that could be further improved is that the straps can creep together resulting in the patient interface becoming misaligned during use. Creep of the straps can potentially undermine the seal between the patient interface and the patient or cause the patient discomfort.

Accordingly, it would be desirable to have a patient interface with a headgear assembly that is capable of maximizing patient comfort. It would also be desirable to have a patient interface with a headgear assembly that is better able to resist misalignment. It would be further desirable to have a system that has a patient interface and headgear assembly wherein each structure is secured to the patient with the optimum force needed to achieve their separate functions. It would be still further desirable to have a headgear assembly that can be secured to the patient's head without applying a continuous force about the patient's head and thereby squeezes the sides of the patient's head inwardly. It would be still yet further desirable to have a headgear assembly that disperses the forces necessary to retain the headgear on the patient's head.

SUMMARY OF THE INVENTION

The object of the present invention is to overcome one or more of the above noted drawbacks currently present in the art. In accordance with the broad teachings of the present invention, a respiratory support system for delivering a breathing gas to a patient is provided. The assembly includes a patient interface to create a substantially airtight seal with the patient. The patient interface may include any one of a number of interfaces such as a mask, mouthpiece, or nasal cannula. The system also includes a headgear assembly that is adapted to be worn by the patient and support the patient interface. The patient interface is coupled to the headgear assembly by a coupling member.

The headgear assembly includes straps fitted about the patient's head and a rigid member sized and shaped to be fitted on the patient. The rigid member assists in keeping the straps appropriately spaced apart so that the straps remain properly located about the patient's head and directed rearwardly.

In another aspect of the present invention, an assembly is provided having a patient interface such as a mask, mouthpiece, or nasal cannula to deliver the breathing gas to the patient. The patient interface also includes a length adjustment assembly and an angle adjustment assembly so that the patient interface can be properly located on the patients face and adjusted to provide the appropriate amount of pressure to create a substantially airtight seal between the patient and the patient interface. The headgear assembly worn by the patient includes straps and webbing. The straps are anchored to a cap having a rigid portion and a pad. Docking members are located on the rigid portion and connect the patient interface to the headgear assembly.

In another aspect of the present invention, a headgear is provided for securing a patient interface to a patient. The headgear includes a rigid member adapted to be worn by the patient having a pad adjacent the rigid member. The patient interface includes a strap that extends substantially linearly between the rigid member and the webbing portion.

These and other features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
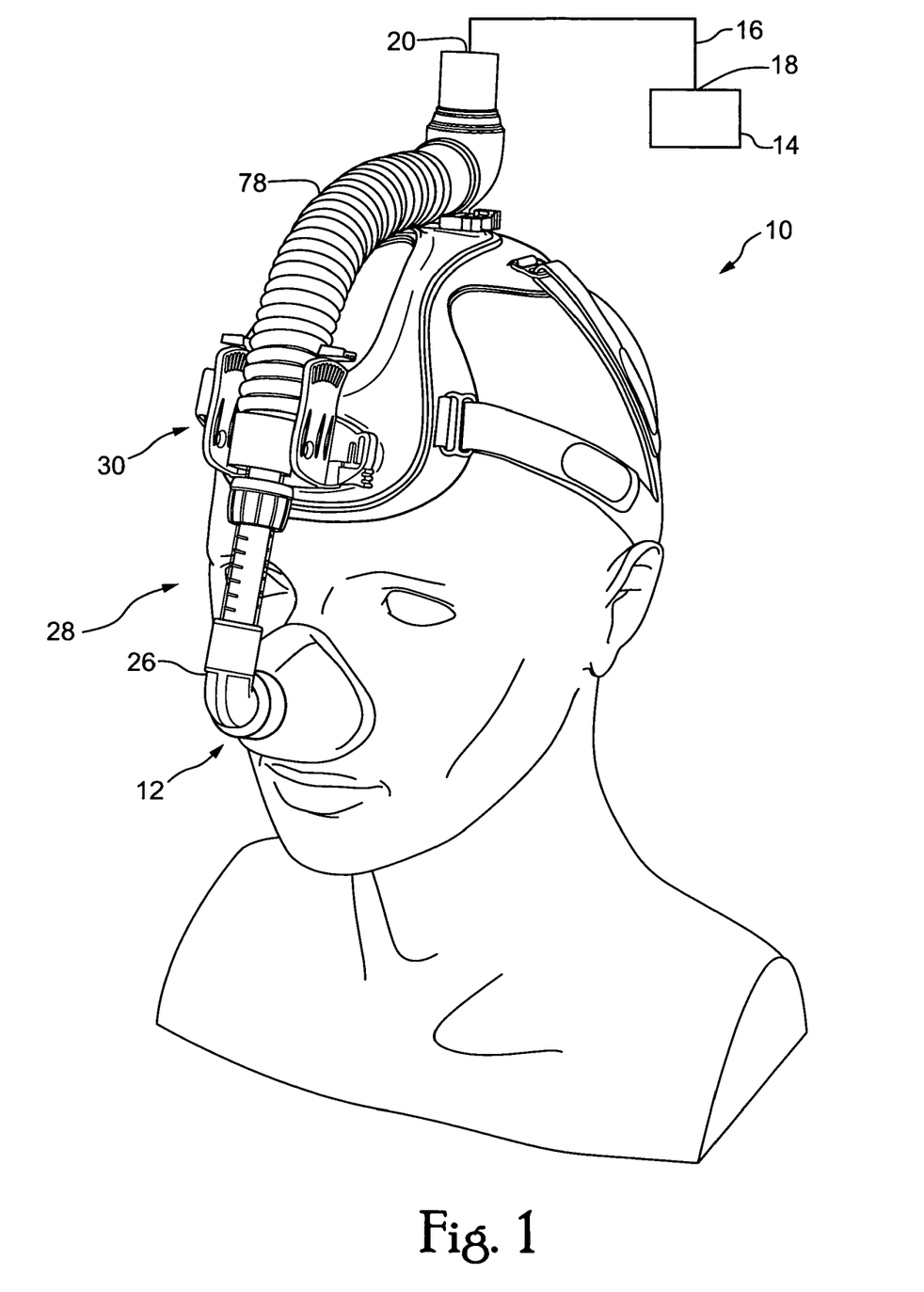
FIG. 1 is a side perspective view of a headgear assembly supporting a patient interface on a patient according to the principles of the present invention.

FIG. 1 illustrates an exemplary embodiment of a headgear assembly 10 according to the principles of the present invention. The headgear assembly 10 supports a patient interface 12 on a patient's head in a respiratory support system. The patient interface 12 communicates a flow of breathing gas between the patient's airway and a pressure generating device 14, such as a ventilator, CPAP device, or variable pressure device, e.g., a BiPAP® device manufactured and distributed by Respironics, Inc. of Pittsburgh, Pa., or an auto-titration pressure support system. A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure generating device 14 is also referred to as a gas flow generating device, because flow results when a pressure gradient is generated.

Communicating a flow of breathing gas between the patient's airway and a pressure generating device 14 includes delivering a flow of breathing gas to the patient from the pressure generating device and exhausting a flow of gas from the patient to ambient atmosphere.

The system for delivering a breathing gas to a patient according to the present invention comprises a pressure or gas flow generating device 14 that produces a flow of gas, a conduit 16, which is also referred to as a patient circuit, having a first end portion 18 operatively coupled to the gas flow generating device and a second end portion 20. Conduit 16 carries the flow of gas from pressure generating device 14 during operation of the system to patient interface device 12 coupled to second end portion 20 of conduit 16.

In the illustrated embodiment the patient interface device 12 is a nasal mask having a cushion. However, the present invention also contemplates that other devices for communicating a flow of gas to an airway of a patient, such as a nasal cannula having prongs, an oral mask, a mouthpiece, or combination nasal/oral masks are suitable for use as patient interface device 12. Of course any suitable device capable of providing a substantially airtight interface with the patient may be used without departing from the novel aspects of the present invention.

Patient interface device 12 also includes an elbow connector 26 that is in turn connected to a length adjustment assembly 28, which adjusts the distance between an angle adjustment assembly 30 and patient interface device 12, to accommodate patients having different facial sizes. As best appreciated with reference to FIG. 2, length adjustment assembly 28 includes a tubular section 32 and an adjustment nut 34. Tubular section 32 is received within adjustment nut 34. A lower end 36 of tubular section 32 is connected to elbow connector 26 using any conventional technique, such as a friction fitting, and the like. Threadings 38 are provided on the exterior of tubular section 32 and on an interior of adjustment nut 34. Length adjustment is accomplished by rotating adjustment nut 34 so that the threadings on adjustment nut 34 engage the threadings on tubular section 32. Rotating adjustment nut 34 causes tubular section 32 to move up or down inside a pivot tube 40 coupled to adjustment nut 34. Pivot tube 40 is part of angle adjustment assembly 30, which is described in greater detail below.

Figures 2, 3:
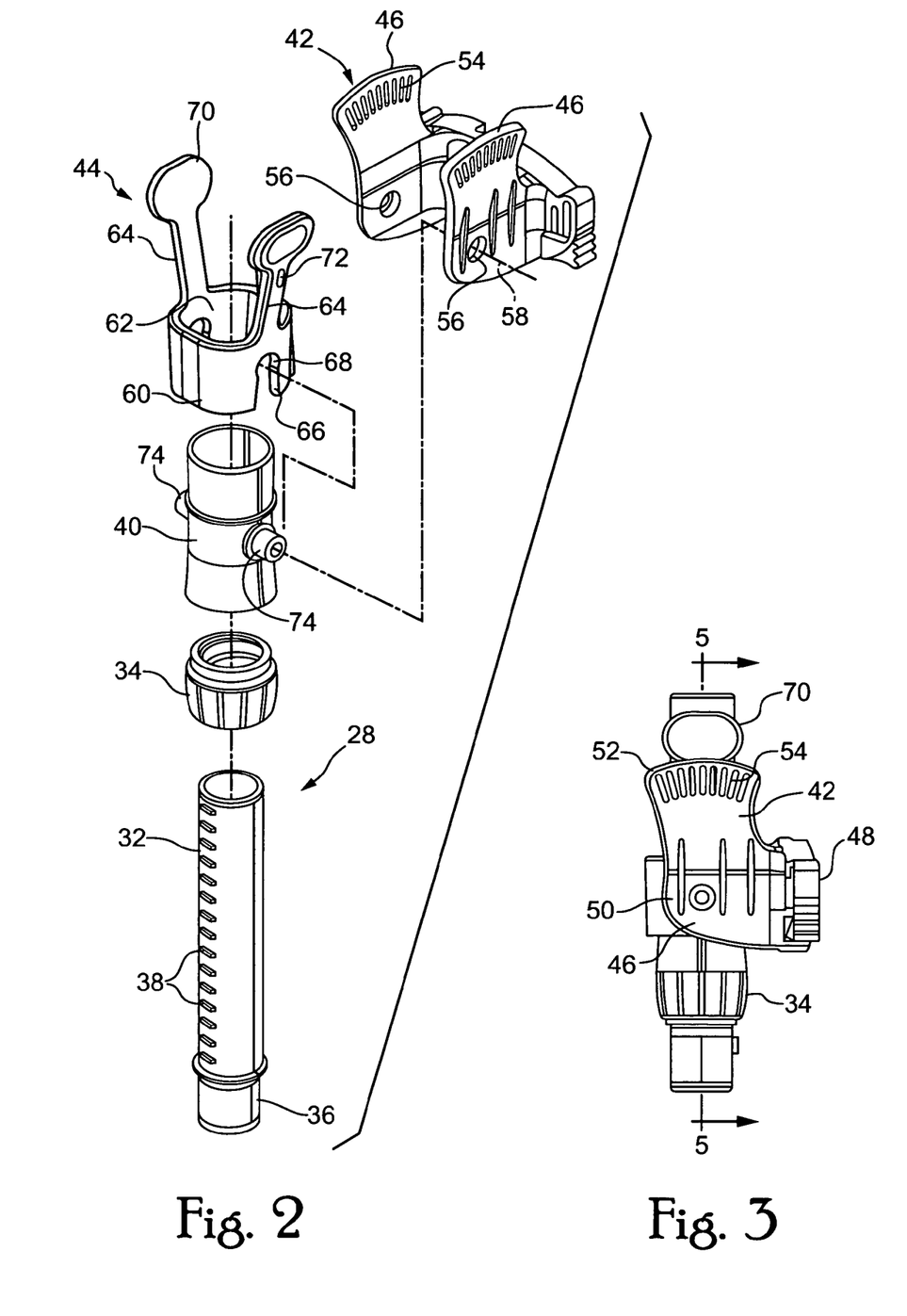
FIG. 2 is an exploded perspective view of a length adjuster and an angle adjuster of the present invention.
FIG. 3 is a side view of the angle adjuster.

Angle adjustment assembly 30, which is best shown in FIGS. 2-3, is a position adjustment mechanism with pre-fixed angular locating positions to control the position or angle of the rigid gas flow conduit relative to the patient's face over a relatively large range of angles, e.g., a 45° range. In addition to this relatively large adjustment capability, angle adjustment assembly 30 provides a force adjustment by means of an integrated spring on a secondary pivoting member over in a narrower range of angles, e.g., 5° range. The angle adjustment assembly allows a cantilevered support to support the patient interface device without a set of headgear straps located at the patient interface device.

Angle adjustment assembly 30 includes an adjustment mechanism that itself includes a mounting bracket 42, an angular pivot housing 44, and the pivot tube 40. Mounting bracket 42 is attached to the headgear 10 as will be explained in more detail below and comprises a pair of substantially parallel mounting bracket arms 46 extending from headgear mounting portions 48. Each mounting bracket arm 46 is substantially L-shaped and extends outward from headgear mounting portions 48 of mounting bracket 42 to a bend portion 50 before extending upwardly to a distal portion 52. Each distal portion 52 includes a plurality of spaced locking/adjustment key holes 54. In the illustrated embodiment, nine key holes 54 are provided on each distal portion 52 corresponding to nine preset positions, which are about 5 degrees apart covering a total angular range of 45 degrees.

Bend portion 50 of each mounting bracket arm 46 includes a pivot hole 56. A pivot axis 58 extends between pivot holes 56 in mounting bracket arms 46. Both angular pivot housing 44 and pivot tube 40 pivot relative to mounting bracket 42 independently about axis 58. Angular pivot housing 44 is mounted between the mounting bracket arms 46 and includes a substantially cylindrical bracket 60 having an interior annular opening 62 and a pair of substantially parallel extension arms 64 extending from opposite sides of cylindrical bracket 60. Cylindrical bracket 60 has a pair of slots 66 terminating at pivot holes 68 corresponding to mounting bracket pivot holes 56. A distal end 70 of each extension arm 64 includes a rigid oval portion functioning as a thumb rest.

On the exterior portion of each extension arm 64, intermediate circular bracket 60 and distal end 70, there is provided an extension key 72 adapted for locking/adjustment engagement with the plurality of locking/adjustment key holes 54 of corresponding mounting bracket arm 46. The angular position of angular pivot housing 44 relative to mounting bracket 42 is locked by two extension keys 72 on extension arms 64 of angular pivot housing 44. In the illustrated embodiment, the locking is dual directional, but could also be a one-directional ratchet type. The angular position of angular pivot housing 44 relative to mounting bracket 42, and thus, the angular position of patient interface device 12 relative to the forehead of the patient, can be released and adjusted by squeezing and moving the two thumb rests at distal ends 70 of extension arms 64 to move extension keys 72 from one angular position to the next and then releasing the thumb rests so locking/adjustment keys 72 are engaged within the desired locking/adjustment key holes 54.

Pivot tube 40 is a rigid tubular member mounted within interior annular opening 62 of circular bracket 60. A pair of pivot projections 74 extend from opposite sides of the exterior of pivot member 40. When assembled, each pivot projection 74 extends through a corresponding circular bracket pivot hole 68 and then through a corresponding mounting bracket arm pivot hole 56. Pivot tube 40 pivots relative to mounting bracket 42, but its motion is restricted by angular pivot housing 44. Pivot tube 40 provides a second range of movement of about 5 degrees.

Figure 4:
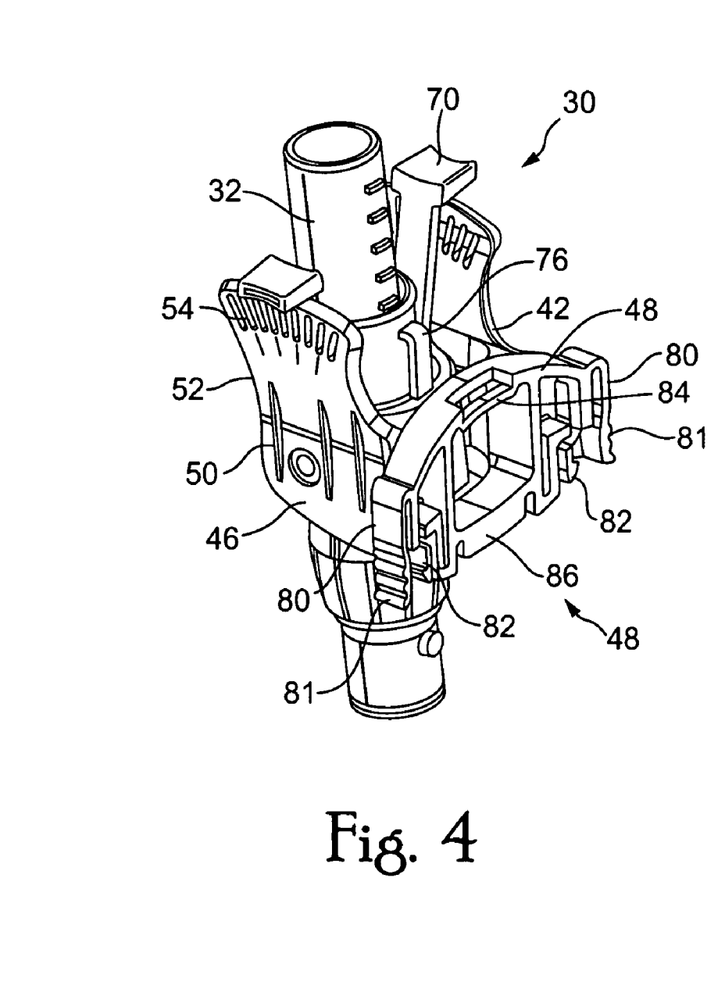
FIG. 4 is a top perspective view of the angle adjuster.
Figure 5:
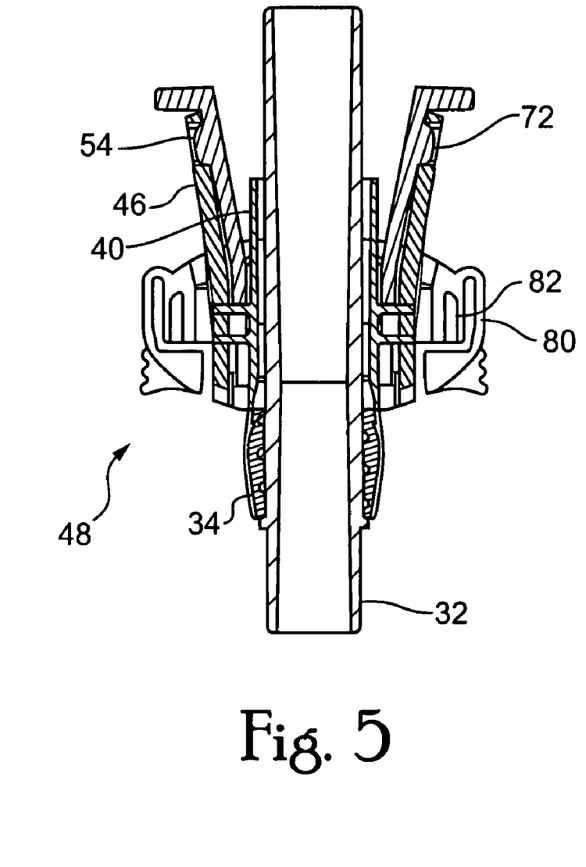
FIG. 5 is a cross-sectional view of the angle adjuster along line 5-5 of FIG. 3.

As shown in FIG. 4, pivot tube 40 is biased by an integrated lever spring 76 provided on circular bracket 60 and intermediate extension arms 64. Pivot tube 40 is pushed inwardly (deflected toward the user when in use) to the most inner position with respect to the angular pivot housing 44 by spring 76. Pivoting of pivot tube 40 against the bias force is limited by contact with the integrated lever spring 76.

Figure 6:
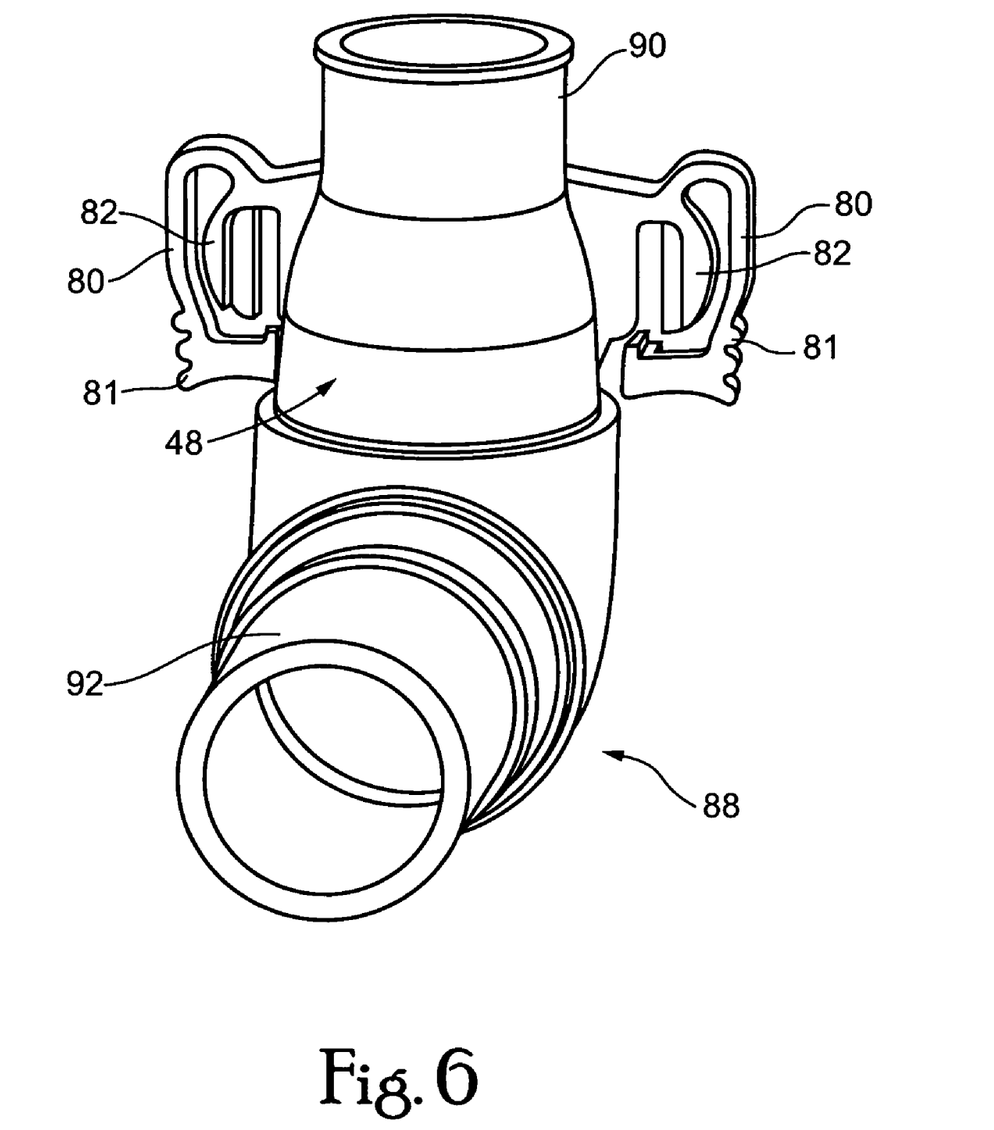
FIG. 6 is a top perspective view of a second elbow.

As shown in FIGS. 1, and 6, patient interface 12 also includes a pipe 78 extending from pivot tube 40. Pipe 78 may be corrugated as shown or may have any of a variety of other configurations as is well known in the art. The pipe terminates at a second elbow 88. The second elbow has a pipe end portion 90 and a conduit end portion 92. Pipe end portion 90 includes a headgear assembly mounting portion 48.

Both mounting portions are similar in construction. The headgear mounting portion 48 on the angle adjustment assembly 30 has a pair of cantilevered arms 80 with a hook or catch 81 and side overhangs 82. The headgear mounting portion 48 also has cantilevered arms 80 with a hook or catch 81 and side overhangs 82. However, headgear mounting portion 48 also has an upper overhang 84 and a lower overhang 86. Collectively overhangs, 82, 84, and 86 operate to provide a rail system to assist in coupling, aligning, and securing headgear mounting portions 48 to headgear assembly 10. The headgear mounting portion 48 on second elbow 88, as seen in FIG. 6, also has a pair of cantilevered arms 80 with a hook or catch 81. The headgear mounting portion 48 also includes corresponding side overhangs 82.

Figure 7:
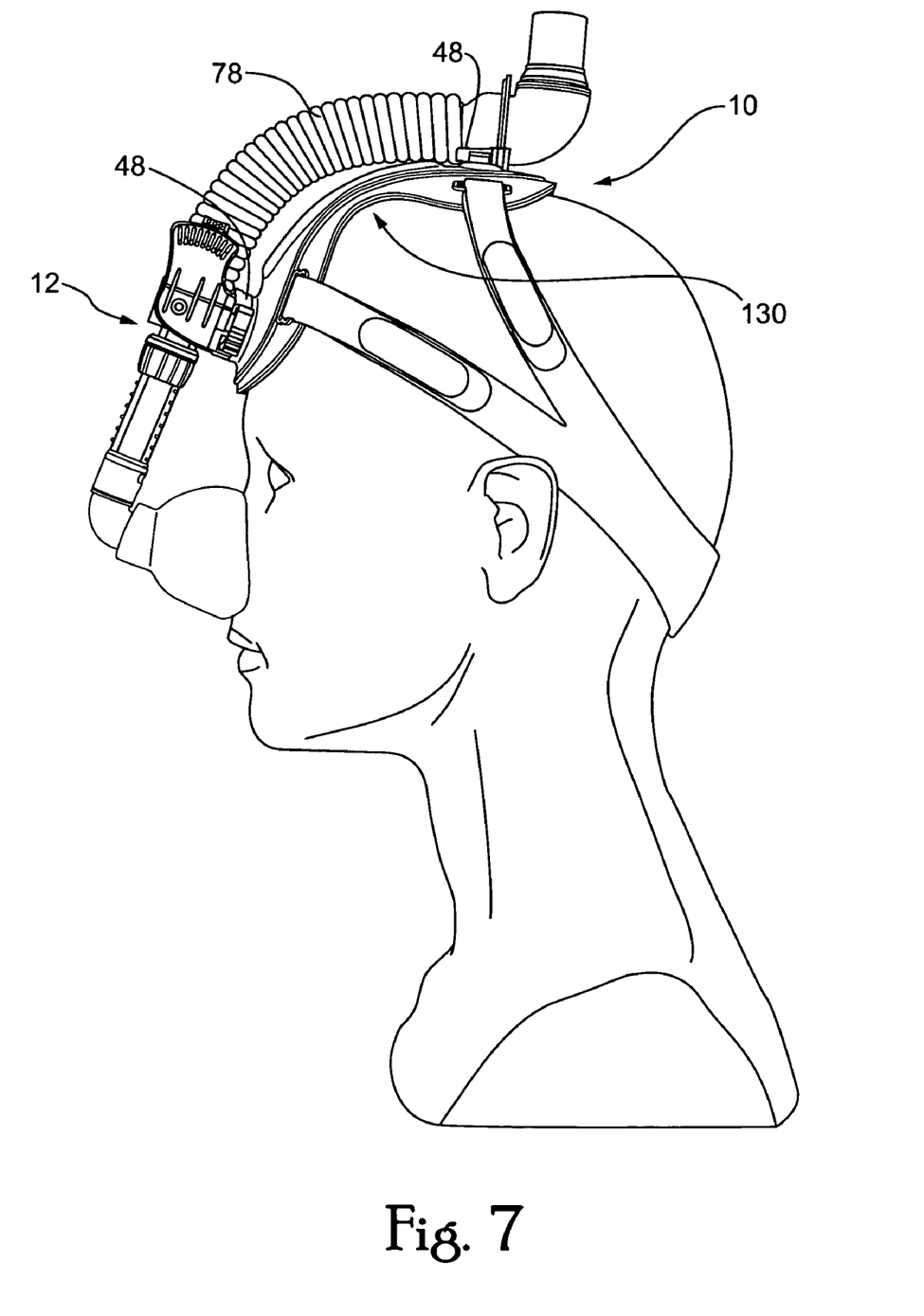
FIG. 7 is a side perspective view of the headgear assembly supporting the patient interface on the patient.
Figure 8:
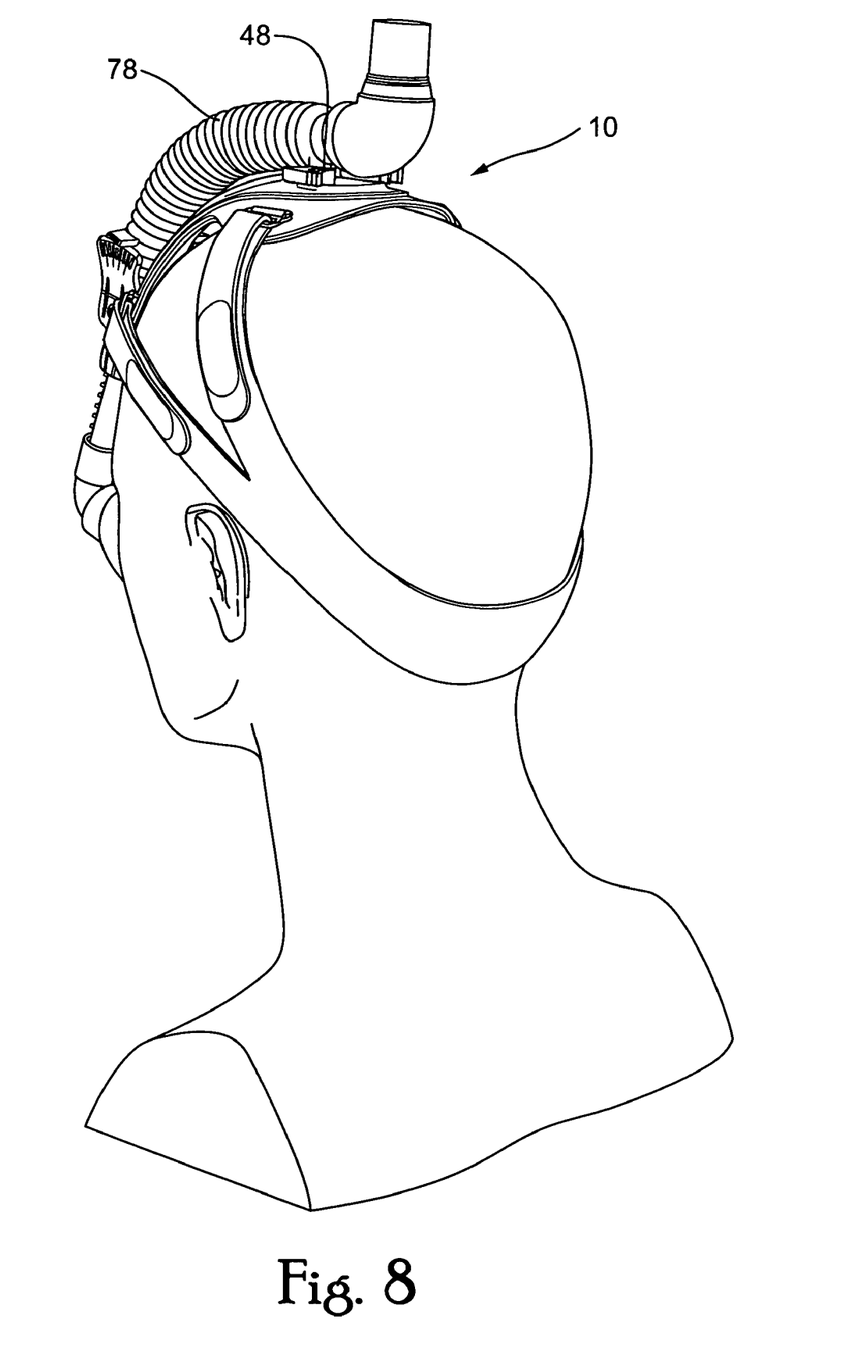
FIG. 8 is rear perspective view of the headgear assembly supporting the patient interface on the patient.
Figures 9, 10:
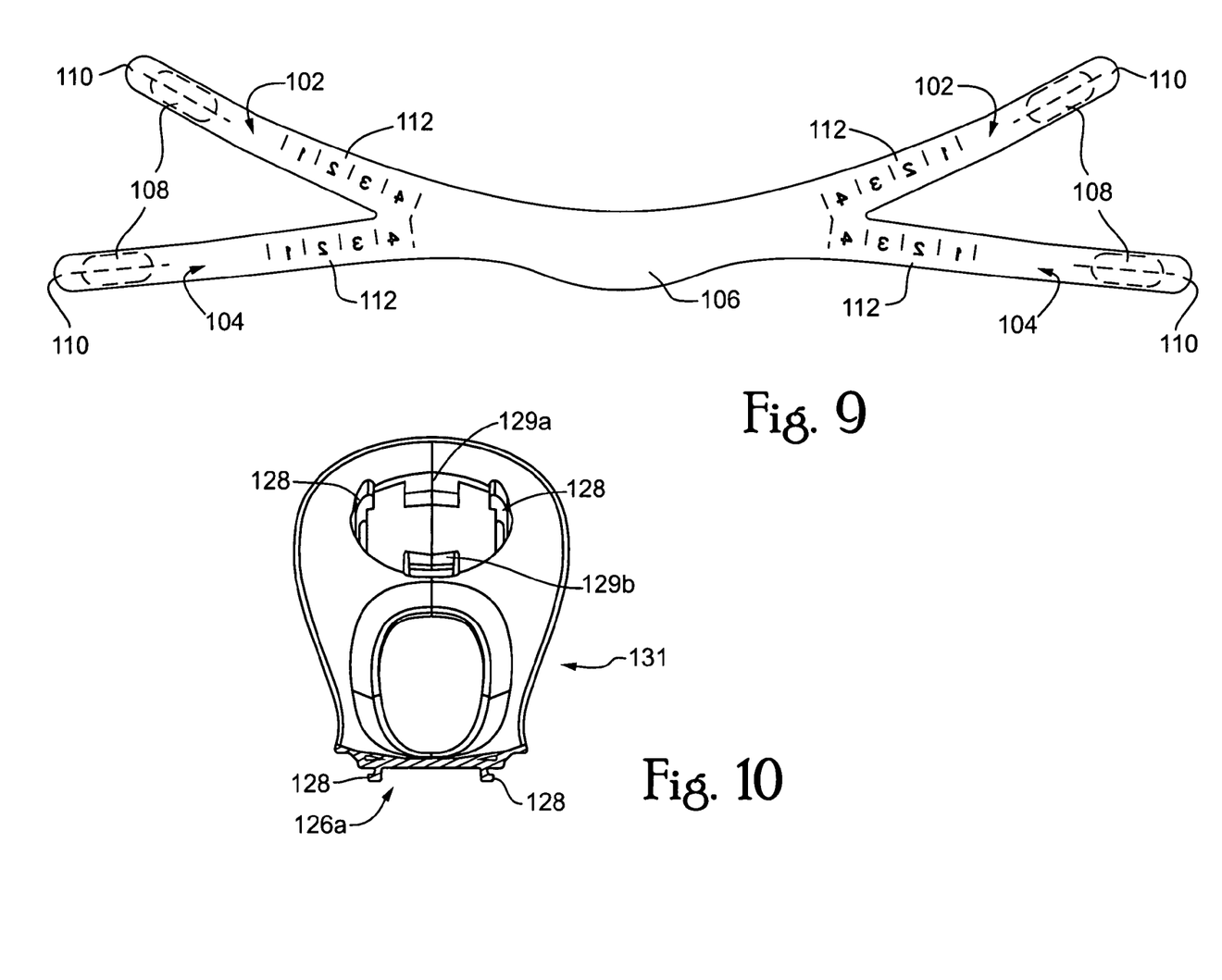
FIG. 9 is a front plan view of a strapping mechanism.
FIG. 10 is a cross-section view of a rigid member along line 10-10 of FIG. 12.
Figure 11:
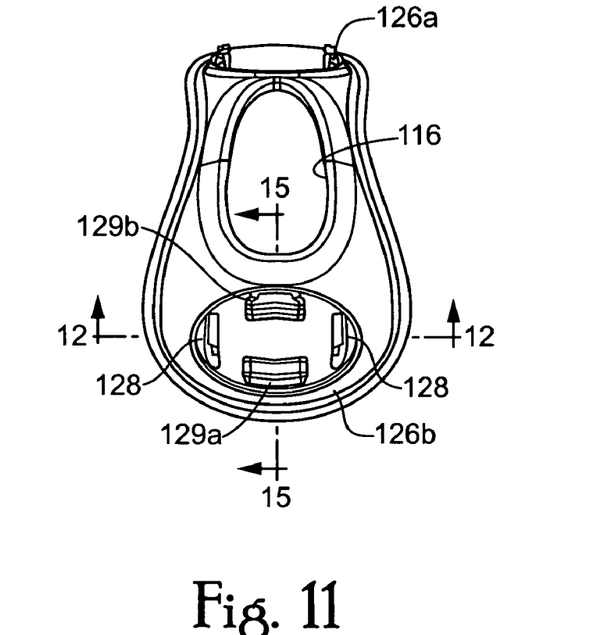
FIG. 11 is a front perspective view of the rigid member.
Figure 12:
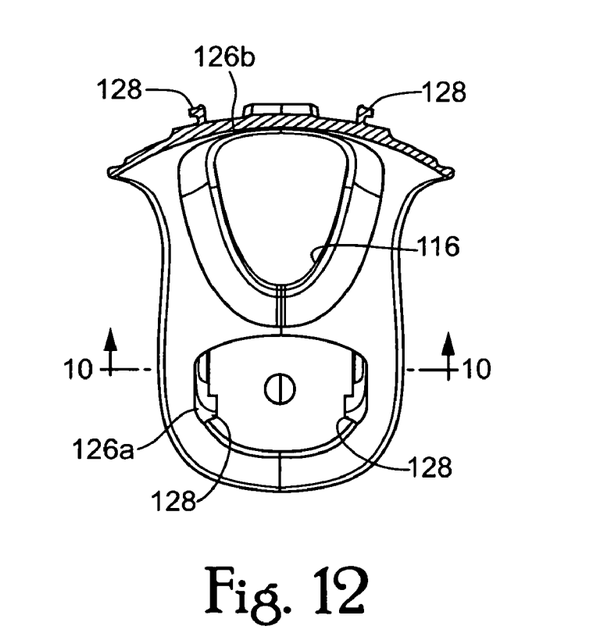
FIG. 12 is a rear perspective view of the rigid member.
Figures 13, 15:
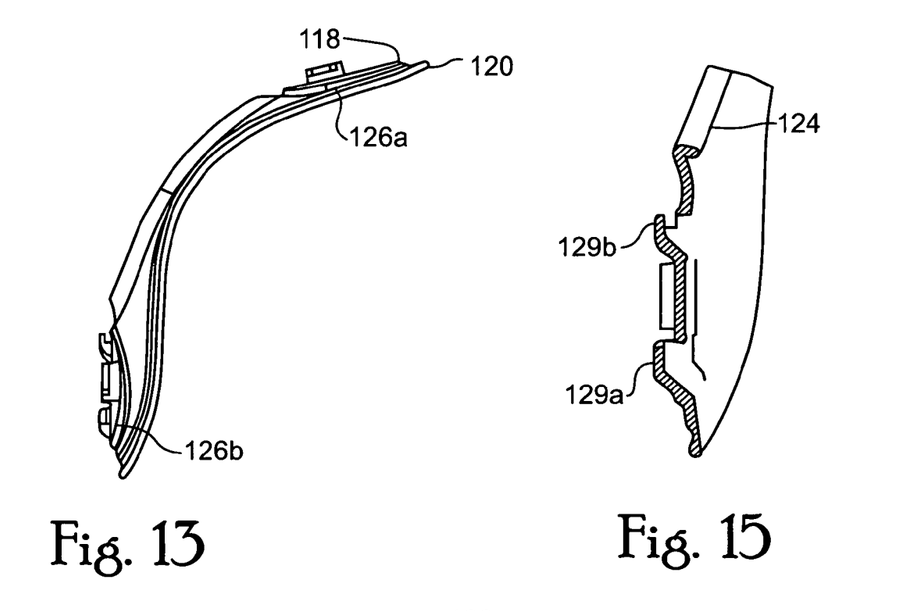
FIG. 13 is a side perspective view of the rigid member.
FIG. 15 is a side cross-sectional view of the rigid member along line 15-15 of FIG. 14.
Figure 14:
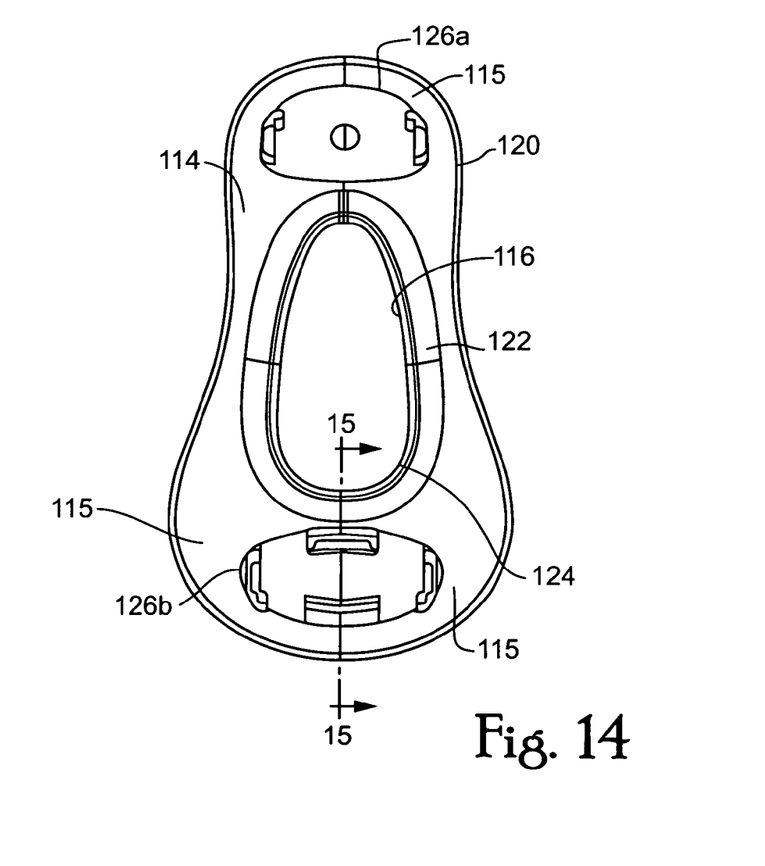
FIG. 14 is a top perspective view of the rigid member.

FIGS. 7-9 show patient interface 12 secured to the novel headgear assembly 10 of the present invention by headgear mounting portions 48. The headgear assembly 10 is adapted to be worn on the head of a patient and includes a strapping mechanism having first straps 102 and second straps 104 joined by webbing 106. Ideally, the webbing 106 is configured to fit or nest below the occipital lobe or protrusion of the patient. Preferably straps 102 and 104 are formed integrally with webbing as seen in FIG. 9. Alternatively, straps 102 and 104 can be formed separately and connected to a separate webbing using any one of a number of different attachment methods. For example straps 102 and 104 could be connected to the webbing by sewing or adhering straps 102 and 104 to webbing 106. Of course, mechanical connectors such as clips, buckles, buttons, pins, snaps, and the like could also be used. Straps 102 and 104 include a hook and loop type fastener 108 at end portions 110 to adjust the functional length of straps 102 and 104. To assist the patient, straps 102 and 104 include indicia 112 so that the proper functional length can be achieved. For instance, as shown in FIG. 9 the indicia are a series of numbers along a portion of straps 102 and 104. End portion 110 of straps 102 and 104 are looped back upon themselves and fastened at some location to create a loop. Indicia 112 ensure that the appropriate functional length can be replicated with respect to each end portion 110 by fastening hook and loop fastener 108 to the corresponding appropriate location on each strap 102 and 104.

Headgear assembly 10 also includes a cap 130 including a rigid member 131 and a pad 132. As best appreciated with reference to FIGS. 10-15, the rigid member has a generally pear-shaped body 114 defining outboard regions 115, and a large opening 116. One of ordinary skill in the art can best appreciate that rigid member 131 may have a variety of other shapes without departing from the scope of the present invention including but not limited to substantially circular, substantially triangular, substantially teardrop shaped, substantially hourglass shaped, substantially square shaped, and the like. About the edge of the body 114 there is a stepped portion 118 terminating at a peripheral edge 120. About opening 116 there is an upturned edge portion 122 terminating at a bead 124. Opening 116 and upturned edge portion 122 provide enhanced comfort to the patient by exposing a greater portion of the patient's head to the external environment. Bead 124 is rounded to remove any sharp edges from this portion of the rigid member.

Rigid member 131 also includes docking portions 126a, 126b. Docking portion 126a, as seen in FIG. 10, is positioned on the rigid member to couple with headgear mounting portion 48 located on second elbow 88. Docking portion 126a has corresponding side overhangs 128 together with overhangs 82 permit headgear mounting portion 48 to be coupled to rigid member 108. Rigid member 131 also has docking portion 126b that is located to couple to headgear mounting potion 48 located on angle adjustment assembly 30. Docking portion 126b has side overhangs 128, upper overhang 129a, and lower overhang 129b. Preferably, rigid member 131 is constructed from a moldable plastic material such as polypropolyne, polyethalene, ABS or other suitable material. The rigid member prevents straps 102 and 104 from creeping together. Accordingly, headgear assembly 10 of the present invention is less likely to become misaligned.

In addition, rigid member serves to disperse the forces exerted on the patient's head by straps 102 and 104. Rather than the straps exerting a continuous force about the patient's head, the present invention disperses these forces over the rigid member. Furthermore, the rigid member serves as an anchor for the straps. Rather than having the straps extend along a curved path about the side of the patient's head, straps 102 and 104 are attached in outboard regions of the rigid member thereby permitting the straps to extend between the cap and the webbing in a substantially linear manner thereby reducing the compressive forces exerted by headgear 10 on the sides of the patient's head.

Figure 16:
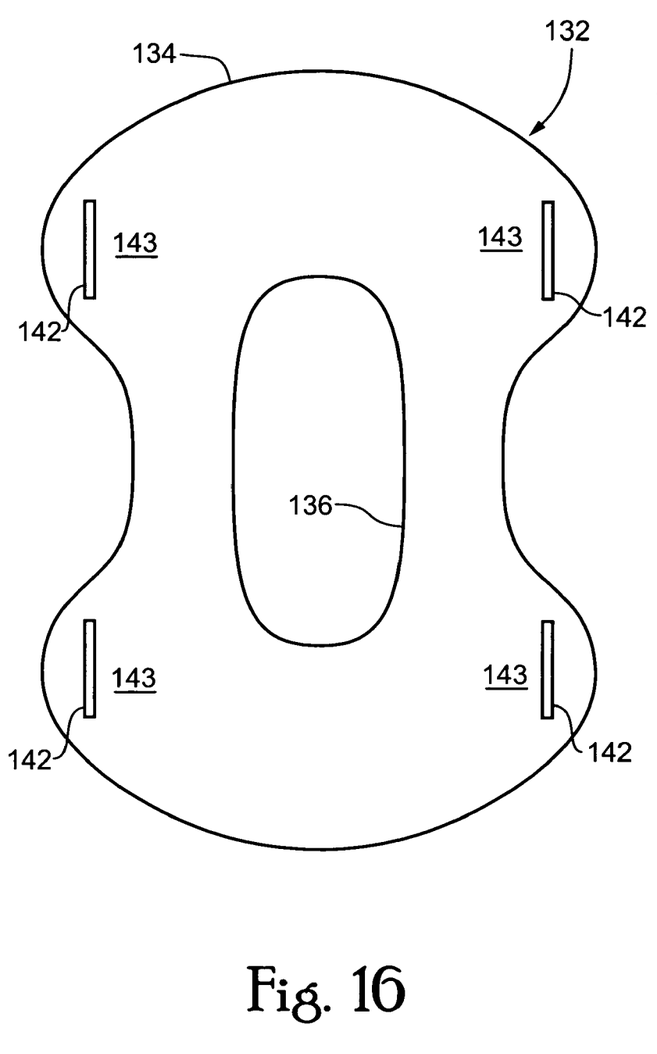
FIG. 16 is a top plan view of a pad.
Figure 17:
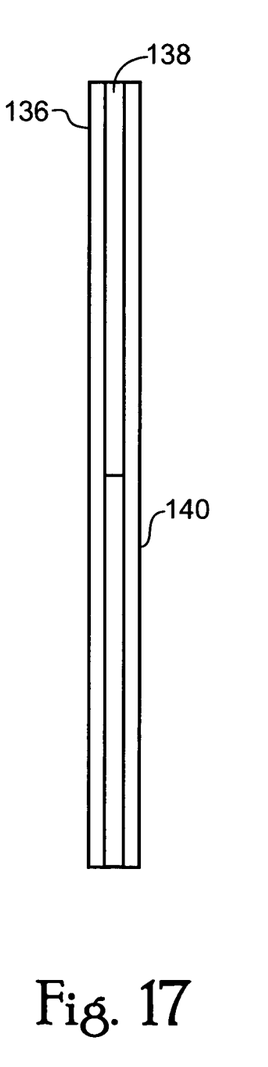
FIG. 17 is a side elevational view of the pad.

As seen in FIG. 16, pad 132 has an hourglass shaped body 134 with an opening 136, and is preferably sized slightly larger than rigid member 131. One of ordinary skill in the art can best appreciate that pad 132 may have a variety of other shapes without departing from the scope of the present invention including but not limited to substantially circular, substantially triangular, substantially teardrop shaped, substantially pear shaped, and substantially square shaped, and the like. In addition, pad 132 could be sized smaller than the rigid member. However, the inventor of the present invention contemplates that having a pad that is slightly oversized relative to rigid member helps to enhance the comfort of the present device by isolating the rigid member from directly contacting the patient's head. Preferably, pad 132 has a layered or laminate construction including an inner layer 136, a middle layer 138, and a top layer 140. However, the inventor presently contemplates that the pad could be constructed of a single layer or multiple layers without departing from the scope of the present invention.

The inner layer is preferably a Thermostat® fabric, the middle layer is preferably a Microban® foam material, and the top layer is preferably an unbreakable loop fabric commonly known by the abbreviation "UBL". Collectively, this construction provides a comfortable, durable pad that inhibits the growth of microbes. In this embodiment, hook and loop fastener 108 is merely the hook portion that may be affixed to the top layer formed from unbreakable loop fabric. Of course, the loop portion could be a small pad attached to straps 102 and 104. Moreover, a variety of other materials could be used without departing from the scope of the present invention. The pad may also include slots 142 formed in outboard regions 143 of pad 132. The slots are sized and shaped to receive straps 102 and 104 to anchor the straps to the pad. The straps are threaded through slots 142 and then fastened back upon themselves by hook and loop fasteners 108 as described above. This location of the slots uniquely allow the straps to be directed in a more linear fashion from pad 132 to webbing 106 rather than having to circumnavigate a curved surface. The result of this feature is that the present invention minimized tangential strapping forces that would squeeze the sides of the patient's head. Therefore, less compressive force is applied and instead the strapping forces are exerted more directly on the webbing 106.

Figure 18:
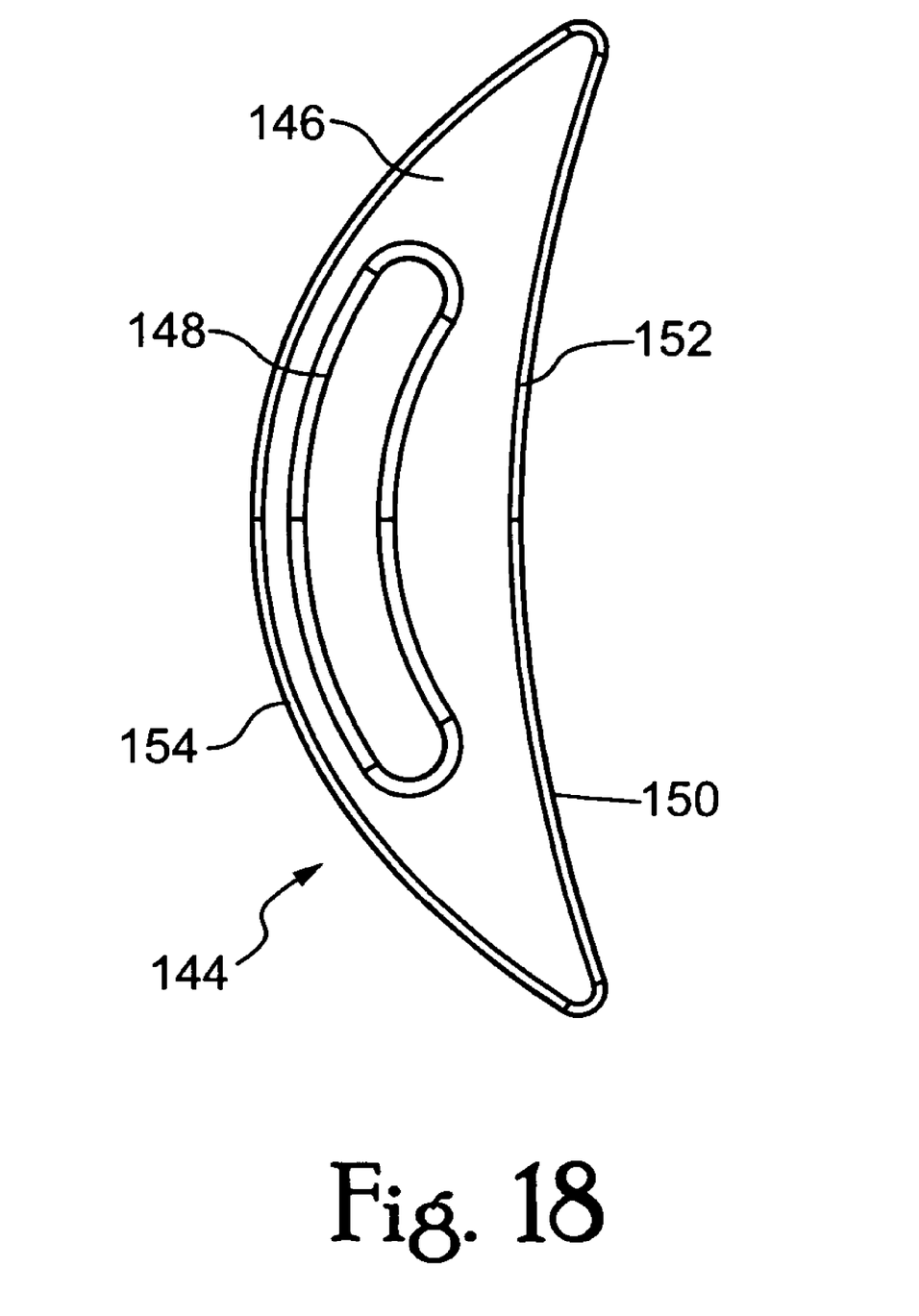
FIG. 18 is a top plan view of an eyelet.

To enhance the wear life of the present invention, the headgear assembly 10 includes eyelets 144. Each eyelet has a body 146 with a central aperture 148 sized so that one of the straps may be fitted through aperture 148 and a peripheral edge 150.

The peripheral edge 150 is defined by an inner edge 152 and an outer edge 154. Eyelets 144 are preferably sewn to pad 132 along inner edge 152. Of course pad 132 could be attached to eyelets 144 and rigid member 131 in a variety of other ways such as by adhesive, tape, and the like. By separating eyelets 144 from rigid member 131 additional flexibility is provided to headgear assembly 10 thereby increasing comfort to the patient.

As shown in FIGS. 1, 7, and 8, the straps may also be held in place with latches 150 rather than by slots 142, or eyelets 144. Of course a variety of other attachment mechanisms could be used without departing from the present invention. For example, straps could be attached by clips, buckles, buttons, pins, snaps, hook and loop fasteners, and the like. In addition, straps 102 and 104 could be fastened to headgear assembly 10 in a variety of other manners. It would also be possible to have a fixed attachment mechanism using adhesive, tape, and the like. In fact, the straps could even be sewn in place. Straps 102 and 104 may be attached at a variety of locations. For example, straps 102 could be attached directly to rigid member 131, directly to pad 132, or directly to pad 132 with eyelets 144. Moreover, the various attachment features could be intermixed with one another on a single device.

In use, the patient can identify the appropriate size of headgear assembly 10 and locate the corresponding indicia 112 on straps 102 and 104. The straps are threaded through the corresponding slot 142, looped back on themselves, and held in place by hook and loop fasteners 108. The patient can then connect the patient interface 12 by connecting headgear mounting portions 48 to the corresponding docks 126a, 126b. Once the second elbow is connected to conduit 16, pressure generating device 14 can then supply pressure to the patient. The headgear assembly of the present invention provides more comfort to the user than provided by prior art devices. Rather than routing the straps 102 and 104 around the patient's head, the present invention routes the straps to the webbing 106 in a more direct manner by anchoring the straps to the pad or rigid member in outboard regions of the pad or rigid member thereby minimizing tangential compressive forces on the user's head. Another unique advantage of the present invention is that the straps are prevented from sliding together. Rigid member 131 keeps straps 102 and 104 from sliding. If the straps were permitted to slide together the headgear assembly 10 could result in discomfort to the user and/or permit the headgear assembly to separate from the patient's head resulting in treatment failure. Furthermore, rigid member 131 distributes the forces exerted by the straps about a larger area of the patient's head than achieved by the straps alone. This feature of the present invention provides further comfort to the user.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. An assembly for use in the delivery of a breathing gas to a patient, comprising:
   (a) patient interface;
   (b) a headgear adapted to be worn by a patient, the headgear comprising:
      (1) a first strap,
      (2) a second strap,
      (3) a web portion connected to the first strap and second strap, and
      (4) a rigid member configured to be located on top of the patient's head connected to the first strap and the second strap such that both the first strap and the second strap interconnect the web portion to the rigid member, wherein the rigid member includes spaced apart first and second portions, wherein the first strap interconnects the first portion to the web portion, wherein the second strap interconnects the second portion to the web portion, and wherein the patient interface is separately connected to the first and the second portions of the rigid member; and
   (c) a coupling member adapted to couple the patient interface to the headgear.

2. The assembly of claim 1, wherein the rigid member has a pear-shaped geometry.

3. The assembly of claim 1, wherein the rigid member includes an opening constructed and positioned to expose a portion of a patient's head to an external environment via the opening.

4. The assembly of claim 1, wherein the patient interface is pivotally connected to the second portion of the rigid member.

5. The assembly of claim 4, wherein the pivotal connection of the patient interface to the second portion of the rigid member comprises:
   a coupling member adapted to couple the patient interface to the headgear, the coupling member including a mounting assembly attached to and located at the second portion, and
   a pivot member attached to the patient interface, the pivot member being pivotably coupled to the coupling member such that the patient interface may be pivoted relative to the mounting assembly.

6. The assembly of claim 1, wherein the rigid member includes an opening constructed and positioned to expose a portion of a patient's head to an external environment via the opening, the opening being disposed between the first and second portions.

7. The assembly of claim 1, wherein the rigid member is constructed and positioned to prevent portions of the first and second straps that are adjacent to the rigid member from creeping toward each other.

8. The assembly of claim 1, wherein:
   the second portion is constructed and arranged to be positioned on a forehead of a patient during use; and
   the first portion is constructed and arranged to be positioned on top of a patient's head during use.

9. The assembly of claim 1, wherein the headgear further includes a pad adjacent the rigid member.

10. The assembly of claim 1, wherein the patient interface is a nasal mask having a cushion, nasal prongs, or a combination thereof.

11. An assembly for use in the delivery of a breathing gas to a patient, comprising:
   (a) a patient interface;
   (b) a headgear adapted to be worn by a patient, the headgear comprising:
      (1) a first strap,
      (2) a second strap,
      (3) a web portion connected to the first strap and second strap, and
      (4) a rigid member configured to be located on top of the patient's head connected to the first strap and the second strap such that both the first strap and the second strap interconnect the web portion to the rigid member, wherein the rigid member includes spaced apart first and second portions, wherein the first strap interconnects the first portion to the web portion, wherein the second strap interconnects the second portion to the web portion, wherein the second portion is constructed and arranged to be positioned on a forehead of a patient during use, and wherein the first portion is constructed and arranged to be positioned on top of a patient's head during use.

12. The assembly of claim 11, wherein the rigid member has a pear-shaped geometry.

13. The assembly of claim 11, wherein the rigid member includes an opening constructed and positioned to expose a portion of a patient's head to an external environment via the opening.

14. The assembly of claim 11, wherein the patient interface is pivotally connected to the second portion of the rigid member.

15. The assembly of claim 14, wherein the pivotal connection of the patient interface to the second portion of the rigid member comprises:

a coupling member adapted to couple the patient interface to the headgear, the coupling member including a mounting assembly attached to and located at the second portion, and a pivot member attached to the patient interface, the pivot member being pivotably coupled to the coupling member such that the patient interface may be pivoted relative to the mounting assembly.

16. The assembly of claim 11, wherein the rigid member includes an opening constructed and positioned to expose a portion of a patient's head to an external environment via the opening, the opening being disposed between the first and second portions.

17. The assembly of claim 11, wherein the rigid member is constructed and positioned to prevent portions of the first and second straps that are adjacent to the rigid member from creeping toward each other.

18. The assembly of claim 11, wherein:
the second portion is constructed and arranged to be positioned on a forehead of a patient during use; and
the first portion is constructed and arranged to be positioned on top of a patient's head during use.

19. The assembly of claim 11, wherein the headgear further includes a pad adjacent the rigid member.

20. The assembly of claim 11, wherein the patient interface is a nasal mask having a cushion, nasal prongs, or a combination thereof.

* * * * *